US00PP12893P2

(12) United States Plant Patent
Moolenaar

(10) Patent No.: US PP12,893 P2
(45) Date of Patent: Aug. 27, 2002

(54) THUNBERGIA PLANT NAMED 'DANIELLA'

(75) Inventor: Alfred Nicol Moolenaar, Voorhout (NL)

(73) Assignee: BCT Bio Chemical Technologies AG, Zug (CH)

( * ) Notice: Subject to any disclaimer, the term of this patent is extended or adjusted under 35 U.S.C. 154(b) by 74 days.

(21) Appl. No.: 09/740,537

(22) Filed: Dec. 20, 2000

(51) Int. Cl.[7] ..... A01H 5/00
(52) U.S. Cl. ..... Plt./226
(58) Field of Search ..... Plt./226

*Primary Examiner*—Bruce R. Campell
*Assistant Examiner*—June Hwu
(74) *Attorney, Agent, or Firm*—C. A. Whealy

(57) ABSTRACT

A new and distinct cultivar of Thunbergia plant named 'Daniella' characterized by its lavender-colored flowers; long peduncles; and dark green leaves.

1 Drawing Sheet

BACKGROUND OF THE INVENTION

The present Invention relates to a new and distinct cultivar of Thunbergia, botanically known as *Thunbergia grandiflora,* and hereinafter referred to by the name 'Daniella'.

The new Thunbergia originated from a cross made by the Inventor of two unidentified selections of *Thunbergia grandiflora.* The cultivar Daniella was discovered and selected by the Inventor as a single plant within the progeny of the stated cross in a controlled environment in Voorhout, The Netherlands in 1997. The selection of this plant was based on its unique flower coloration.

Asexual reproduction of the new Thunbergia by cuttings taken in a controlled environment in Voorhout, The Netherlands, has shown that the unique features of this new Thunbergia are stable and reproduced true to type in successive generations.

SUMMARY OF THE INVENTION

The new Thunbergia has not been observed under all possible environmental conditions. The phenotype may vary somewhat with variations in environment such as temperature, daylength, light intensity, nutritional and water status without, however, any variance in genotype.

The following traits have been repeatedly observed and are determined to be the unique characteristics of 'Daniella'. These characteristics in combination distinguish 'Daniella' as a new and distinct cultivar:

1. Lavender-colored flowers.
2. Long peduncles.
3. Dark green leaves.

BRIEF DESCRIPTION OF THE PHOTOGRAPH

The accompanying colored photograph illustrates the overall appearance of the new Thunbergia. This photograph shows the colors as true as it is reasonably possible to obtain in colored reproductions of this type. Colors in the photograph may differ slightly from the color values cited in the detailed botanical description, which accurately describe the colors of the new Thunbergia. The photograph comprises a side perspective view of a typical plant of 'Daniella'.

DETAILED BOTANICAL DESCRIPTION

The aforementioned and following observations, measurements and values describe plants grown in a glass-covered greenhouse in Voorhout, The Netherlands, during the winter under conditions which approximate commercial production practices. After the cuttings were rooted, plants were planted in 17-cm containers and grown for about eight months with day and night temperatures about 18 to 21° C. In the following description, color references are made to The Royal Horticultural Society Colour Chart except where general terms of ordinary dictionary significance are used.

Botanical classification: *Thunbergia grandiflora* cultivar Daniella.

Parentage: Seedling from cross-pollination of two unidentified selections of *Thunbergia grandiflora,* not patented.

Propagation:
- *Type.*—By cuttings.
- *Time to initiate roots.*—About 42 days at 21° C.
- *Time to develop roots.*—About 70 days at 21° C.
- *Root description.*—Fine and freely branching.

Plant description:
- *Plant form.*—Upright and climbing; plants require support. Plants require pinching to enhance branching; pinching results in the development of about 5 lateral branches.
- *Plant vigor.*—Vigorous. Suitable for 17 to 22-cm containers.
- *Plant height.*—About 3 to 4 m.
- *Plant width.*—About 50 cm.
- *Lateral branch description.*—Length: Up to 4 m. Diameter: About 7 mm. Internode length: About 25 cm. Texture: Pubescence, coarse. Color: 137B to 137C with a very weak reddish flush, most prominent at the nodes.

Foliage description:
- *Arrangement.*—Opposite, single.
- *Quantity per lateral branch.*—Up to 40.
- *Length.*—About 17 cm.
- *Width.*—About 12 cm.
- *Shape.*—Cordate.
- *Apex.*—Acuminate.
- *Base.*—Cordate.
- *Margin.*—Entire.

*Texture.*—Pubescence on both surfaces; rough and coarse.

*Color.*—Young leaves, upper surface: Close to 147A. Young leaves, lower surface: More gray than 189A. Fully expanded leaves, upper surface: Darker than 147A. Fully expanded leaves, lower surface: 189A.

*Petiole.*—Length: About 6 cm. Diameter: About 2.5 mm. Color: Grayish medium green close to 138A with some purplish anthocyanin on the upper surface.

Flower description:

*Flowering habit.*—Single trumpet-shaped flowers; axillary, solitary or in racemes; corolla five-lobed. Typically about 5 to 20 flowers and flower buds per lateral branch and up to 100 open flowers and flower buds per plant. Flowering begins about two months after planting. Flowers not persistent. Not fragrant.

*Natural flowering season.*—Plants flower year-round in greenhouses in The Netherlands.

*Flowers.*—Diameter: About 9 cm. Depth (height): About 3.5 cm. Longevity on the plant: About 6 days.

*Flower buds: Shape: Ellipsoidal. Length: About* 4 cm. Diameter: About 1.5 cm. Color: White, close to 155D, with flush of light blue, close to 97C to 97D.

*Petals.*—Arrangement: Five in a single whorl; fused at base. Lobe shape: Broadly elliptic to rounded. Apex: Rounded. Margin: Entire, occasionally incised. Length: About 3.5 cm. Width: About 4 cm. Color: When opening, upper surface: 91A to 91B. When opening, lower surface: 97C to 97D. Fully opened, upper surface: 91A to 91B; becoming 91B with subsequent development. Fully opened, lower surface: 97D. Throat: 5C to 5D.

*Flower bracts.*—Arrangement: Two, cupped-shaped. Shape: Ovate, convex. Apex: Acute to acuminate. Margin: Entire. Length: About 3 cm. Width: About 2 cm. Color, both surfaces: Slightly darker than 147C.

*Peduncles.*—Aspect: About 90° to stem. Strength: Strong. Length: About 5.5 cm. Color: 137B to 137C.

*Reproductive organs.*—Stamens: Quantity: Four. Anther shape: Linear. Anther length: About 10 mm. Anther diameter: About 2 mm. Anther color: Creamy white; towards apex, 158B, with fine hairs, 164B; towards base, 86A pubescence, initially white becoming brownish with development. Pollen: None observed. Pistils: Quantity: One. Pistil length: About 3 cm. Stigma shape: Bilobed. Stigma color: Creamy white close to 155A. Style length: About 2.5 cm. Style color: 58A.

*Seed.*—Seed production has not been observed.

Disease resistance: Plants of the new Thunbergia have not been observed to be resistant to pathogens common to Thunbergias.

Weather tolerance: Plants of the new Thunbergia are very tolerant to rain and wind.

It is claimed:

1. A new and distinct Thunbergia plant named 'Daniella' as illustrated and described.

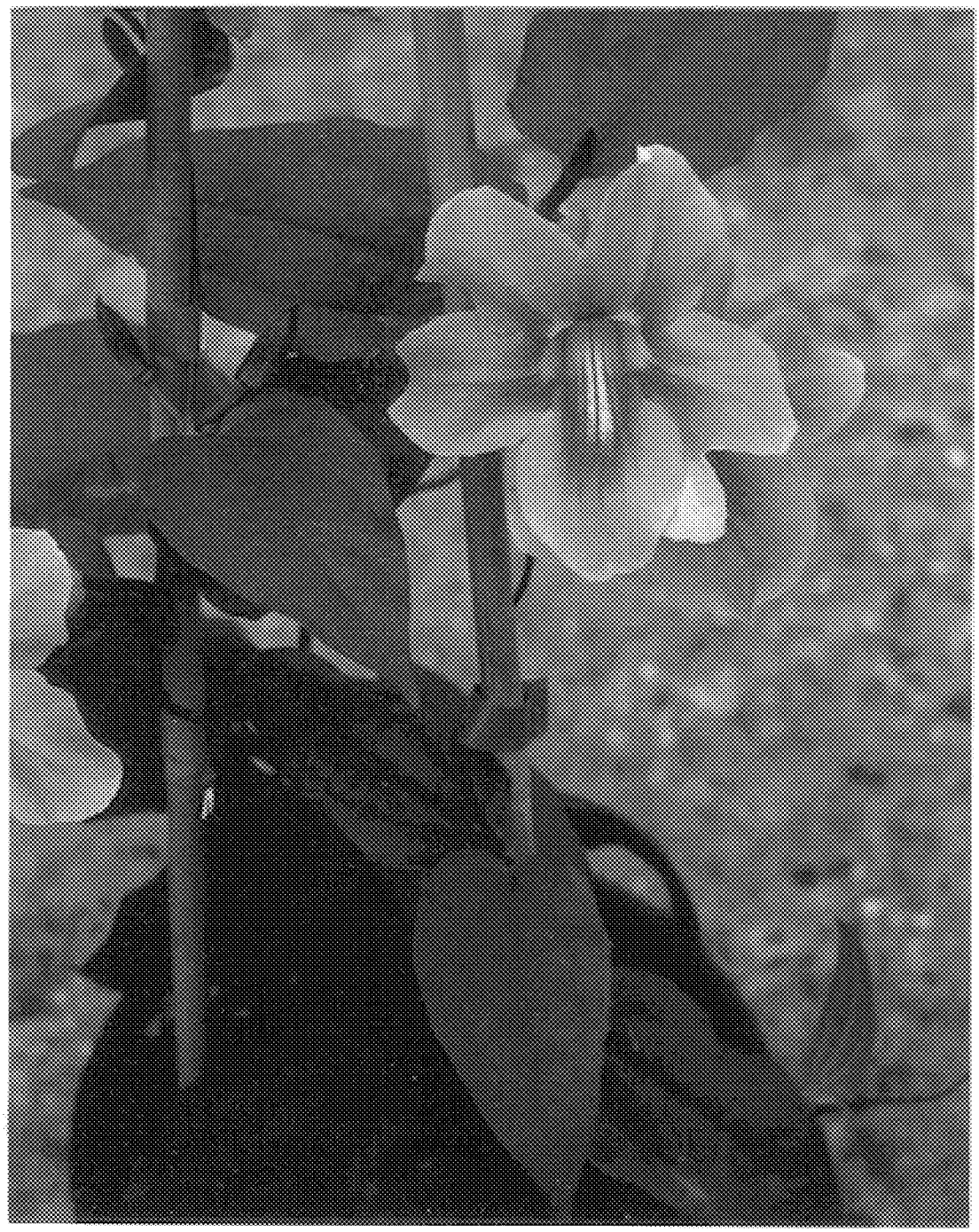

* * * * *